US011628130B2

(12) United States Patent
Morishima

(10) Patent No.: US 11,628,130 B2
(45) Date of Patent: Apr. 18, 2023

(54) CLEANSER COMPOSITION

(71) Applicant: KAO CORPORATION, Tokyo (JP)

(72) Inventor: Atsumi Morishima, Sumida-ku (JP)

(73) Assignee: KAO CORPORATION, Tokyo (JP)

( * ) Notice: Subject to any disclaimer, the term of this patent is extended or adjusted under 35 U.S.C. 154(b) by 61 days.

(21) Appl. No.: 16/633,923

(22) PCT Filed: Jul. 24, 2018

(86) PCT No.: PCT/JP2018/027619
§ 371 (c)(1),
(2) Date: Jan. 24, 2020

(87) PCT Pub. No.: WO2019/022046
PCT Pub. Date: Jan. 31, 2019

(65) Prior Publication Data
US 2021/0145720 A1    May 20, 2021

(30) Foreign Application Priority Data

Jul. 25, 2017   (JP) .............................. JP2017-143589

(51) Int. Cl.
| | | |
|---|---|---|
| *A61K 8/46* | (2006.01) | |
| *A61K 8/34* | (2006.01) | |
| *A61Q 5/02* | (2006.01) | |
| *A61Q 19/10* | (2006.01) | |
| *A61K 8/41* | (2006.01) | |
| *A61K 8/42* | (2006.01) | |

(52) U.S. Cl.
CPC .............. *A61K 8/463* (2013.01); *A61K 8/342* (2013.01); *A61K 8/416* (2013.01); *A61K 8/42* (2013.01); *A61Q 5/02* (2013.01); *A61Q 19/10* (2013.01); *A61K 2800/596* (2013.01)

(58) Field of Classification Search
None
See application file for complete search history.

(56) References Cited

U.S. PATENT DOCUMENTS 4,859,456 A * 8/1989 Marschner ............. A61K 8/416
424/47
2012/0052032 A1* 3/2012 Yamaki .................... A61Q 5/04
424/70.1

| | | | |
|---|---|---|---|
| 2014/0079658 | A1 | 3/2014 | Terazaki et al. |
| 2014/0079660 | A1 | 3/2014 | Doi |
| 2014/0080746 | A1 | 3/2014 | Doi et al. |
| 2015/0174024 | A1 | 6/2015 | Doi et al. |
| 2015/0202133 | A1 | 7/2015 | Doi et al. |

FOREIGN PATENT DOCUMENTS

| | | |
|---|---|---|
| CN | 104603251 A | 5/2015 |
| CN | 104661634 A | 5/2015 |
| CN | 104955933 A | 9/2015 |
| EP | 2 899 258 A1 | 7/2015 |
| EP | 2 952 566 A1 | 12/2015 |
| JP | 63-161078 A | 7/1988 |
| JP | 2008-231034 A | 10/2008 |
| JP | 2015-27974 A | 2/2015 |
| JP | 2015-27976 A | 2/2015 |
| JP | 2015-178467 A | 10/2015 |

OTHER PUBLICATIONS

JP201527976 Eng Tran. Published: Feb. 12, 2015.*
European Patent Office Communication and extended search report issued in the corresponding European Patent Application No. 18838229.5 dated Mar. 23, 2021.
International Search Report, issued in PCT/JP2018/027619, dated Sep. 25, 2018.

* cited by examiner

*Primary Examiner* — Nicole P Babson
*Assistant Examiner* — Lori K Mattison
(74) *Attorney, Agent, or Firm* — Birch, Stewart, Kolasch & Birch, LLP

(57) ABSTRACT

A cleansing composition that simultaneously provides excellent washing performance and a good care feeling while securing good stability without being influenced by the use environment. The cleansing composition includes components (A) to (C): (A) an internal olefin sulfonate having 12 or more and 24 or less of carbon atoms: 1.8 mass % to 20 mass %; (B) a cationic surfactant represented by a specific formula: 0.1 mass % to 8 mass %; and (C) an aliphatic alcohol having 12 or more and 22 or less of carbon atoms: 1 mass % to 20 mass %, wherein a mass ratio of the content of the component (B) to component (A), (B)/(A), is 0.1 to 1, and a mass ratio of the content of the component (C) to the total of the components (A) and (B), (C)/{(A)+(B)}, is 0.1 to 4.5 or less.

11 Claims, No Drawings

CLEANSER COMPOSITION

FIELD OF THE INVENTION

The present invention relates to a cleansing composition.

BACKGROUND OF THE INVENTION

In cleansing compositions which are used for washing skin or hair or the like, anionic surfactants are heavily used, which are suitable for providing good foaming and a sufficient volume of foam, etc. and ensuring high washing performance. Such cleansing compositions are required by imparting a smooth feel and a moist feeling to the application site such as skin or hair not only during washing but also after washing, and providing a good care feeling, and a variety of developments have been performed.

For example, Patent Literature 1 discloses a cleansing composition in which two specific internal olefin sulfonates as an anionic surfactant are used in combination. The composition enhances the sense of, for example, a refreshing feeling without a tenseness, while exhibiting good foaming performance. Patent Literatures 2 and 3 disclose cleansing compositions for skin or hair in which a specific internal olefin sulfonate, a specific oil, and an anionic surfactant are used in combination, and which are applied to hair shampoo or body shampoo. The cleansing composition imparts hair manageability after drying, reduces greasy to skin, and gives a moist feeling, while, for example, retaining good foam durability and rinsability.

PATENT LITERATURE (Patent Literature 1) JP-A-2015-178467
(Patent Literature 2) JP-A-2015-27974
(Patent Literature 3) JP-A-2015-27976

SUMMARY OF THE INVENTION

The present invention relates to a cleansing composition comprising the following components (A) to (C):

(A) an internal olefin sulfonate having 12 or more and 24 or less of carbon atoms: 1.8 mass % or more and 20 mass % or less;

(B) a cationic surfactant represented by the following formula (b-1) or (b-2): 0.1 mass % or more and 8 mass % or less,

$R^1CONH(CH_2)_nN(R^2)_2$ (b-1)

wherein $R^1$ represents an aliphatic hydrocarbon group having 11 to 23 carbon atoms; $R^2$ represents a hydrogen atom or an alkyl group having 1 to 4 carbon atoms; and n represents an integer of 2 to 4,

wherein $R^3$ represents a linear or branched alkyl group or alkenyl group having 10 to 22 carbon atoms; $R^4$, $R^5$, and $R^6$ each independently represent a linear or branched alkyl group having 1 to 3 carbon atoms; and $Z^-$ represents an anionic group being a counterion for an ammonium salt; and (C) an aliphatic alcohol having 12 or more and 22 or less of carbon atoms: 1 mass % or more and 20 mass % or less, wherein the mass ratio of the content of the component (B) to the content of the component (A), (B)/(A), is 0.1 or more and 1 or less; and the mass ratio of the content of component the (C) to the total content of the component (A) and the component (B), (C)/{(A)+(B)}, is 0.1 or more and 4.5 or less.

As seen above, cleansing compositions are required by various inventivenesses for enhancing, for example, a desired moist feeling while ensuring high washing performance by using anionic surfactants. There is also greater difficulty in ensuring stability of the composition itself. For example, in trying of use especially in areas where the hardness of water is high, it should also be considered that the volume of foam tends to decrease, and it should also be taken into consideration that the stability of a composition may be deteriorated as the use temperature increases.

However, even the compositions including specific internal olefin sulfonates as anionic surfactants as described in Patent Literatures 1 to 3 do not sufficiently have both high washing performance and a good care feeling, while retaining the stability of the composition without being influenced by such a variable use environment. Therefore, there is still room for improvement.

That is, the present invention relates to a cleansing composition which can simultaneously provide excellent washing performance and a good care feeling while securing good stability without being influenced by the use environment which may variously vary.

Accordingly, the present inventor variously studied, and consequently found that a cleansing composition which can simultaneously provide excellent washing performance and a good care feeling while securing good stability without being influenced by the use environment, by using a specific amount of a specific internal olefin sulfonate and further using a specific cationic surfactant and an aliphatic alcohol in a predetermined quantitative relationship.

According to the cleansing composition of the present invention, it can not only retain good stability without causing separation of components even when stored in a high temperature range but also can impart a good care feeling to the application site, such as skin or hair, while securing a large volume of foam even in use of high-hardness water and exhibiting excellent washing performance.

Accordingly, the cleansing composition of the present invention is a composition which is highly useful as a cleansing composition for skin or a cleansing composition for hair, which have both excellent washing performance and a care feeling without being influenced by the use environment.

DETAILED DESCRIPTION OF THE INVENTION

The present invention will now be described in detail.
The cleansing composition of the present invention comprises the following components (A) to (C):

(A) an internal olefin sulfonate having 12 or more and 24 or less of carbon atoms: 1.8 mass % or more and 20 mass % or less;

(B) a cationic surfactant represented by the following formula (b-1) or (b-2): 0.1 mass % or more and 8 mass % or less, $R^1CONH(CH_2)_nN(R^2)_2$ (b-1)

wherein R¹ represents an aliphatic hydrocarbon group having 11 to 23 carbon atoms; R² represents a hydrogen atom or an alkyl group having 1 to 4 carbon atoms; and n represents an integer of 2 to 4,

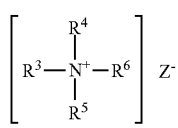

(b-2)

wherein R³ represents a linear or branched alkyl group or alkenyl group having 10 to 22 carbon atoms; R⁴, R⁵, and R⁶ each independently represent a linear or branched alkyl group having 1 to 3 carbon atoms; and Z⁻ represents an anionic group being a counterion for an ammonium salt; and (C) an aliphatic alcohol having 12 or more and 22 or less of carbon atoms: 1 mass % or more and 20 mass % or less, wherein the mass ratio of the content of the component (B) to the content of the component (A), (B)/(A), is 0.1 or more and 1 or less; and the mass ratio of the content of the component (C) to the total content of the component (A) and the component (B), (C)/{(A)+(B)}, is 0.1 or more and 4.5 or less.

In the present specification, the "care feeling" means softness or a moist feeling which is felt at the application site, such as skin or hair, after the use of the cleansing composition of the present invention, and means a feel obtained by a conditioning effect as also referred to as a "skin care feeling" in skin or referred to as a "hair care feeling" in hair.

The cleansing composition of the present invention contains 1.8 mass % or more and 20 mass % or less of an internal olefin sulfonate having 12 or more and 24 or less of carbon atoms as the component (A). The internal olefin sulfonate of the component (A) is a sulfonate prepared by sulfonation, neutralization, and hydrolysis of an internal olefin (an olefin having a double bond inside the olefin chain) as a raw material. The term "internal olefin" is a broad meaning encompassing a case containing a trace amount of so-called α-olefin having a double bond at 1-position of the carbon chain. That is, sulfonation of internal olefin quantitatively generates β-sultone, the β-sultone partially changes to γ-sultone and olefin sulfonic acid, and they are further converted into a hydroxyalkane sulfonate and an olefin sulfonate in a neutralization-hydrolysis process (for example, J. Am. Oil Chem. Soc. 69, 39 (1992)). Here, the hydroxy group of the resulting hydroxyalkane sulfonate is present inside the alkane chain, and the double bond of the olefin sulfonate is present inside the olefin chain. In addition, the resulting product is mainly a mixture thereof, and as a part thereof, a trace amount of a hydroxyalkane sulfonate having a hydroxy group at the end of the carbon chain or an olefin sulfonate having a double bond at the end of the carbon chain may be included. In the present specification, each of these products and a mixture thereof are collectively referred to as an internal olefin sulfonate (component (A)). In addition, a hydroxyalkane sulfonate is referred to as a hydroxy form of internal olefin sulfonate (hereinafter, also referred to as HAS), and an olefin sulfonate is referred to as an olefin form of internal olefin sulfonate (hereinafter, also referred to as IOS).

The number of carbon atoms of the internal olefin sulfonate of the component (A) is 12 or more, preferably 14 or more, and more preferably 16 or more from the viewpoint of improving foam durability and rinsability. In addition, the number of carbon atoms of the internal olefin sulfonate of the component (A) is 24 or less, preferably 20 or less, and more preferably 18 or less from the viewpoint of giving an excellent care feeling, such as softness and moist feeling, while showing high washing performance by expression a sufficient volume of foam and giving a refresh cleansing feel (feeling after cleansing) at the application site, such as skin or hair. The number of carbon atoms of the internal olefin sulfonate contained in the component (A) is 12 or more and 24 or less, preferably 14 or more and 20 or less, and more preferably 16 or more and 18 or less. The hydroxy form and the olefin form having these various carbon atom numbers are derived from internal olefins used as raw materials, and a hydroxy form and an olefin form having carbon atom numbers other than the above-mentioned numbers may be included.

When the component (A) includes an internal olefin sulfonate having 16 carbon atoms and an internal olefin sulfonate having 18 carbon atoms, the total content of the internal olefin sulfonate having 16 carbon atoms and the internal olefin sulfonate having 18 carbon atoms in the component (A) is preferably 50 mass % or more, more preferably 60 mass % or more, further preferably 70 mass % or more, further preferably 80 mass % or more, more preferably 90 mass % or more, and further preferably 95 mass % or more from the viewpoint of high foam quality durability. The upper limit of the total content is 100 mass %.

When the component (A) includes an internal olefin sulfonate having 16 carbon atoms and an internal olefin sulfonate having 18 carbon atoms, the mass ratio of the content of the internal olefin sulfonate having 16 carbon atoms to the content of the internal olefin sulfonate having 18 carbon atoms, (internal olefin sulfonate having 16 carbon atoms)/(internal olefin sulfonate having 18 carbon atoms), is not particularly limited, and may be 100/0 or 0/100. In particular, from the viewpoint of retaining high foam quality, the mass ratio is preferably 50/50 to 99/1, more preferably 60/40 to 95/5, further preferably 70/30 to 90/10, further preferably 75/25 to 90/10, further preferably 75/25 to 85/15, and further preferably 78/22 to 85/15.

The mass ratio can be measured by high-performance liquid chromatography mass spectrometry (hereinafter, abbreviated to HPLC-MS). Specifically, the internal olefin sulfonate having 16 carbon atoms and the internal olefin sulfonate having 18 carbon atoms are separated from the component (A) or the resulting cleansing composition by HPLC and can be each identified by MS, and the mass ratio can be determined from the HPLC-MS peak areas.

The sulfonate group of the internal olefin sulfonate of the component (A) is present in the carbon chain of the internal olefin sulfonate, i.e., inside the olefin chain or the alkane chain, as obvious from the above-described method, and as a part thereof, a trace amount of a sulfonate group present at the end of the carbon chain may be included.

The content of the internal olefin sulfonate having a sulfonate group at 2-position in the component (A) is preferably 25 mass % or less, more preferably 24 mass % or less, further preferably 23 mass % or less, and further preferably 22 mass % or less, preferably 21 mass % or less, more preferably less than 20 mass %, further preferably 19 mass % or less, further preferably 18 mass % or less, and preferably 17.6 mass % or less from the viewpoint of simultaneously achieving securing of a sufficient volume of foam and rinsability. In addition, the content of the internal olefin sulfonate having a sulfonate group at 2-position in the component (A) is preferably 5 mass % or more, more preferably 6 mass % or more, further preferably 7 mass % or more, further preferably 8 mass % or more, and preferably 9 mass % or more from the viewpoint of reducing producing cost and improving productivity. Furthermore, the content of the internal olefin sulfonate having a sulfonate group at 2-position in the component (A) is preferably 5 mass % or more and 25 mass % or less, preferably 5 mass % or more and 24 mass % or less, preferably 5 mass % or more and 23 mass % or less, preferably 5 mass % or more and 22 mass % or less, preferably 5 mass % or more and 21 mass % or less, more preferably 6 mass % or more and less than 20 mass %, further preferably 7 mass % or more and 19 mass % or less, further preferably 8 mass % or more and 18 mass % or less, and more preferably 9 mass % or more and 17.6 mass % or less from the viewpoint described above.

The content of the internal olefin sulfonate having a sulfonate group at 2-position in the component (A) can be measured by a method such as nuclear magnetic resonance spectrometry. Specifically, it can be measured by a method using gas chromatography described in the example described below.

In addition, the content of the olefin sulfonate having the sulfonate group at 1-position of the olefin chain or the alkane chain in the component (A) is preferably 3.0 mass % or less, more preferably 2.5 mass % or less, further preferably 2.0 mass % or less, further preferably 1.5 mass % or less, and more further preferably 1.0 mass % or less from the viewpoint of suppressing precipitation at low temperature, and the lower limit of the content is preferably 0 mass % from the viewpoint of reducing producing cost and improving productivity.

The internal olefin sulfonate is preferably a mixture of a hydroxy form and an olefin form. The mass ratio of the content of the hydroxy form of the internal olefin sulfonate to the content of the olefin form of the internal olefin sulfonate, (hydroxy form)/(olefin form), in the component (A) or the cleansing composition of the present invention is preferably 50/50 to 100/0, more preferably 60/40 to 100/0, further preferably 70/30 to 100/0, further preferably 75/25 to 100/0, and more preferably 75/25 to 95/5 from the viewpoint of improving producibility and reducing impurities.

The mass ratio of the content of the hydroxy form of the internal olefin sulfonate to the content of the olefin form of the internal olefin sulfonate in the component (A) or the cleansing composition of the present invention can be measured by separating the hydroxy form and the olefin form from the component (A) or the resulting cleansing composition by HPLC and then by the method described in the example.

The content of the component (A) is 1.8 mass % or more and preferably 2.0 mass % or more in the cleansing composition of the present invention from the viewpoint of securing good cleansing properties and foamability without being influenced by the use environment, such as the temperature and the hardness of water to be used. In addition, the content of the component (A) is 20 mass % or less, preferably 8.5 mass % or less, and more preferably 5.5 mass % or less from the viewpoint of giving a good care feeling together with the component (B). The content of the component (A) is 1.8 mass % or more and 20 mass % or less, preferably 2.0 to 8.5 mass %, and more preferably 2.0 to 5.5 mass % in the cleansing composition of the present invention.

The internal olefin sulfonate (A) can be prepared by sulfonating an internal olefin having 12 or more and 24 or less of carbon atoms and then performing neutralization and then hydrolysis. The conditions for the sulfonation, neutralization, and hydrolysis are not particularly limited, and, for example, the conditions described in Japanese Patent No. 1633184, Japanese Patent No. 2625150, or Tenside Surf. Det., 31 (5), 299 (1994) can be referred to.

The raw material internal olefin in the present invention is an olefin having a double bond inside the olefin chain as described above. The number of carbon atoms of the raw material internal olefin is preferably 12 to 24, more preferably 12 to 20, more preferably 12 to 18, more preferably 14 to 18, and further preferably 16 to 18 from the viewpoint of the performance of the internal olefin sulfonate of the resulting component (A). As the internal olefin to be used, a single internal olefin may be used, or a combination of two or more internal olefins may be used.

The content of the internal olefin having a double bond at 2-position in the raw material internal olefin is preferably 40 mass % or less, more preferably 35 mass % or less, further preferably 32 mass % or less, preferably 30 mass % or less, and preferably 27 mass % or less from the viewpoint of using it as an index in preparation of the target internal olefin sulfonate by sulfonation of the raw material internal olefin. The lower limit of the content is preferably 5 mass % or more, more preferably 6 mass % or more, further preferably 7 mass % or more, further preferably 8 mass % or more, further preferably 9 mass % or more, further preferably 12 mass % or more, and further preferably 15 mass % or more. The content of the internal olefin having a double bond at 2-position in the raw material internal olefin is preferably 5 mass % or more and 40 mass % or less, preferably 5 mass % or more and 35 mass % or less, preferably 5 mass % or more and 32 mass % or less, preferably 5 mass % or more and 30 mass % or less, preferably 6 mass % or more and 30 mass % or less, preferably 7 mass % or more and 30 mass % or less, preferably 8 mass % or more and 30 mass % or less, preferably 9 mass % or more and 30 mass % or less, preferably 12 mass % or more and 30 mass % or less, and preferably 15 mass % or more and 27 mass % or less from the viewpoint described above.

In addition, the content of so-called α-olefin, an olefin having a double bond at 1-position in the raw material internal olefin, is preferably 3.0 mass % or less, more preferably 2.5 mass % or less, further preferably 2.0 mass % or less, further preferably 1.5 mass % or less, and more further preferably 1.0 mass % or less, and the lower limit of the content is preferably 0 mass % from the viewpoint of reducing producing cost and improving productivity.

The distribution of double bonds in the raw material internal olefin can be measured by the method described in the example using a gas chromatograph-mass spectrometer (hereinafter, abbreviated to GC-MS). Specifically, components having different carbon chain lengths and double bond positions are each precisely separated with a gas chromatography apparatus (hereinafter, abbreviated to GC). Each component is applied to a mass spectrometer (hereinafter, abbreviated to MS) to identify the double bond position thereof, and the rate of each component can be determined from its GC peak area. Specifically, the measurement is possible by the method described in the example below.

The sulfonation reaction can be performed by reacting 1.0 to 1.2 mol of sulfur trioxide gas to 1 mol of the raw material internal olefin. The reaction can be performed at a temperature of 20° C. to 40° C.

The neutralization is performed by reacting 1.0 to 1.5 mol times the molar amount of an alkali aqueous solution, such as sodium hydroxide, ammonia, or 2-aminoethanol with the theoretical amount of the sulfonate group.

The hydrolysis reaction may be performed in the presence of water at 90° C. to 200° C. for 30 minutes to 3 hours. These reactions can be performed successively. In addition, after completion of the reactions, purification by, for example, extraction and washing, can be performed.

In producing of the internal olefin sulfonate (A), the sulfonation, neutralization, and hydrolysis treatments may be performed using a raw material internal olefin having a distribution of carbon atom numbers of 12 to 24 or may be performed using a raw material internal olefin having a single number of carbon atoms. In addition, as needed, a mixture of internal olefin sulfonates having different numbers of carbon atoms produced in advance may be used.

Since the internal olefin sulfonate (A) used in the present invention can be prepared by sulfonation, neutralization, and hydrolysis of an internal olefin as described above, in producing of the component (A), unreacted raw material internal olefin and inorganic compound may remain. It is preferred that the contents of these components are much smaller.

The content of the unreacted internal olefin and the content of the inorganic compound can be measured by the method described in the example below.

The cleansing composition of the present invention contains 0.1 mass % or more and 8 mass % or less of a cationic surfactant represented by the following formula (b-1) or (b-2) as the component (B). The component (B) contained in such an amount, as a cationic surfactant, can effectively enhance the finger combability of hair during washing and the slipperiness of hair after drying or can effectively enhance the moist feeling of skin after washing when used together with an aliphatic alcohol of the component (C) described below.

The cationic surfactant as component (b-1) represented by the following formula (b-1) is a so-called amide amine compound or a salt thereof,

$$R^1CONH(CH_2)_nN(R^2)_2 \quad (b\text{-}1)$$

wherein $R^1$ represents an aliphatic hydrocarbon group having 11 to 23 carbon atoms, $R^2$ represents a hydrogen atom or an alkyl group having 1 to 4 carbon atoms, and n represents an integer of 2 to 4.

Examples of the $R^1CO$ in the formula (b-1) include a lauroyl group, a myristoyl group, a palmitoyl group, a stearoyl group, an oleoyl group, and behenoyl group. Examples of the group represented by $R^2$ include a methyl group, an ethyl group, and a propyl group, and a methyl group and an ethyl group are particularly preferred. n preferably represents 2 or 3.

The component (b-1) is specifically one or more selected from the group consisting of dimethylaminoethylamide stearate, dimethylaminopropylamide stearate, diethylaminoethylamide stearate, diethylaminopropylamide stearate, dipropylaminoethylamide stearate, dipropylaminopropylamide stearate, dimethylaminoethylamide palmitate, dimethylaminopropylamide palmitate, dimethylaminoethylamide myristate, dimethylaminopropylamide myristate, dimethylaminoethylamide behenate, and dimethylaminopropylamide behenate. In particular, diethylaminoethylamide stearate and dimethylaminopropylamide stearate are preferred from the viewpoint of enhancing the slipperiness of hair after drying or the moist feeling of skin after washing when used together with the component (C), while effectively securing the stability of the composition.

The cationic surfactant of the component (b-2) is represented by the following formula (b-2):

wherein $R^3$ represents a linear or branched alkyl group or alkenyl group having 10 to 22 carbon atoms, $R^4$, $R^5$, and $R^6$ each independently represent a linear or branched alkyl group having 1 to 3 carbon atoms, and $Z^-$ represents an anionic group being a counterion for an ammonium salt.

$R^3$ preferably represents a linear or branched alkyl group or alkenyl group having 16 to 22 carbon atoms and more preferably represents a linear alkyl group. In addition, $R^4$, $R^5$, and $R^6$ preferably each represent a methyl group. Examples of the anionic group represented by $Z^-$ include halide ions, such as a chloride ion and a bromide ion; and organic anions, such as an ethyl sulfate ion and a methyl carbonate ion. In particular, halide ions, such as a chloride ion, are particularly preferred, and a chloride ion is more preferred.

Specifically, the component (b-2) is preferably a mono long chain alkyl quaternary ammonium salt having 10 to 22 carbon atoms and more preferably a mono long chain alkyl quaternary ammonium salt having 16 to 22 carbon atoms and is more specifically one or more selected from the group consisting of cetyltrimethylammonium chloride, stearyltrimethylammonium chloride, arachyl trimethyl ammonium chloride, and behenyltrimethylammonium chloride. In particular, behenyltrimethylammonium chloride is preferred from the viewpoint of imparting slipperiness and softness to hair after drying or from the viewpoint of imparting a moist feeling to skin after washing when used together with the component (C).

The content of the component (B) is 0.1 mass % or more, preferably 1.0 mass % or more, and further preferably 1.5 mass % or more in total in the cleansing composition of the present invention from the viewpoint of imparting slipperiness and softness to hair after drying or from the viewpoint of imparting a moist feeling to skin after washing when used together with the component (C). In addition, the content of the component (B) is 8 mass % or less and preferably 2.0 mass % or less in the cleansing composition of the present invention from the viewpoint of the stability of the cleansing composition. The content of the component (B) is 0.1 mass % or more and 8 mass % or less, preferably 1.0 to 2.0 mass %, and more preferably 1.5 to 2.0 mass % in total in the cleansing composition of the present invention.

The mass ratio of the content of the component (B) to the content of the component (A), (B)/(A), is 0.1 or more, preferably 0.3 or more, and 1 or less, preferably 0.9 or less, from the viewpoint of securing a satisfactory volume of foam. The mass ratio of the content of the component (B) to the content of the component (A), (B)/(A), is 0.1 or more and 1 or less, preferably 0.1 to 0.9, and more preferably 0.3 to 0.9.

The cleansing composition of the present invention contains 1 mass' or more and 15 mass % or less of an aliphatic alcohol having 12 or more and 22 or less of carbon atoms as the component (C). Consequently, it is possible to secure a sufficient volume of foam even upon application of high-hardness water and to effectively enhance also the durability.

The aliphatic alcohol of the component (C) preferably has 16 or more and 22 or less of carbon atoms and more preferably has an alkyl group having 16 or 18 carbon atoms. This alkyl group is preferably a linear alkyl group and is specifically one or more selected from the group consisting of cetyl alcohol, stearyl alcohol, arachyl alcohol, and behenyl alcohol. In particular, cetyl alcohol and stearyl alcohol are preferred.

The content of the component (C) is 1 mass % or more, preferably 2.4 mass % or more, and further preferably 3.6 mass % or more in the cleansing composition of the present invention from the viewpoint of satisfactorily securing foam volume and its durability even when high-hardness water is used. In addition, the content of the component (C) is 20 mass % or less in the cleansing composition of the present invention from the viewpoint of easiness of application of the composition and is preferably 15 mass % or less and more preferably 11 mass % or less from the viewpoint of securing, together with the component (B), giving an excellent care feeling. In addition, the content of the component (C) is 1 mass % or more and 20 mass % or less, preferably 1 mass % or more and 15 mass % or less, more preferably 2.4 to 15 mass %, further preferably 2.4 to 11 mass %, and further preferably 3.6 to 11 mass % in the cleansing composition of the present invention.

The mass ratio of the content of the component (C) to the total content of the component (A) and the component (B), (C)/{(A)+(B)}, is 0.1 or more, preferably 0.5 or more, and more preferably 0.9 or more and 4.5 or less, preferably 3.5 or less, more preferably 3.3 or less, and further preferably 2.4 or less from the viewpoint of securing good stability of the cleansing composition even when stored in a high temperature range. In addition, the mass ratio of the content of the component (C) to the total content of the component (A) and the component (B), (C)/{(A)+(B)}, is 0.1 or more and 4.5 or less, preferably 0.5 to 3.5, more preferably 0.9 to 3.3, and further preferably 0.9 to 2.4.

Although the cleansing composition of the present invention can appropriately contain a surfactant other than the component (A) and the component (B), from the viewpoint of securing a sufficient volume of foam without being influenced by the use environment and also securing a good care feeling while showing excellent washing performance, the cleansing composition can contain an anionic surfactant other than the component (A) within a range capable of also retaining the stability of the composition. The content of the anionic surfactant other than the component (A) is preferably 0.1 to 10 mass %, more preferably 0.1 to 5 mass %, in the cleansing composition of the present invention. Examples of the anionic surfactant other than the component (A) include fatty acids, alkyl ether acetates, alkylsarcosines, alkylglycines, alkylalanines, sulfosuccinic acid, sodium polyoxyethylene lauryl ether sulfates, α-olefin sulfonic acid, secondary alkane sulfonates, linear alkylbenzene sulfonates, alkyl isethionates, and alkyl sulfoacetates; and salts thereof.

The cleansing composition of the present invention can appropriately contain, in addition to the above-mentioned components, components which are used in general cleansing compositions within a range which does not impair the effects of the present invention. Examples of such other components include a viscosity reducer, a preservative, a reducing agent, a feel improver, a thickener, a flavoring agent, a UV absorber, a visible light absorber, a chelating agent, an antioxidant, a coloring agent, a preservative, a pH adjuster, a viscosity adjuster, a pearlescent agent, and a moistening agent, in addition to water which can be used as a medium in producing the component (A).

The viscosity at 30° C. of the cleansing composition of the present invention is preferably 500 to 30,000 mPa·s, more preferably 500 to 10,000 mPa·s, and further preferably 1,000 to 5,000 mPa·s from the viewpoint of effectively giving a good care feeling while more effectively enhancing the washing performance by forming a sufficient volume of foam and the viewpoint of enhancing, for example, the application properties to an application site.

Since the cleansing composition of the present invention can form a sufficient volume of foam without being influenced by the hardness of water to be used and retain the excellent washing performance, it is possible to simultaneously achieve excellent washing performance and a good care feeling while securing a sufficient volume of foam even when medium to high hardness water, which generally gradually decreases the volume of foam, is used. Medium to high hardness water means water having a hardness of about 6° dH or more.

In addition, the cleansing composition of the present invention may be in any dosage form and can be in an arbitrary form, such as liquid, foam, paste, or cream. In particular, a liquid, paste, or cream form is preferred, and a paste or cream form is more preferred, from the viewpoint of effectively expressing performance for simultaneously securing a sufficient volume of foam and giving a good care feeling without being influenced by the use environment. In a liquid form, in addition to water as a liquid medium, for example, polyethylene glycol or ethanol may be used. The content of the water is preferably 10 mass % or more and 95 mass % or less in the cleansing composition of the present invention.

The cleansing composition of the present invention can be suitably used as a so-called skin cleansing composition which is used for washing skin or as a so-called hair cleansing composition which is used for washing hair from the viewpoint of forming a sufficient volume of foam without being influenced by the use environment to show excellent washing performance and being capable of giving, to the application site, such as skin or hair, good slipperiness and softness after washing in the case of hair or a moist feeling after washing in the case of skin. In addition, since the cleansing composition of the present invention has both washing performance and a care feeling, treatment for imparting softness and a moist feeling to the applied site is not required to be separately performed, washing and care of the application site can be performed by a single process, and a cleansing effect and a conditioning effect can be simultaneously given.

Examples of the skin cleansing composition include body shampoo, facial cleanser, a makeup remover, and hand soap. Examples of the hair cleansing composition include hair shampoo and a cleansing conditioner. In particular, from the viewpoint of showing performance for simultaneously giving a cleansing effect and a conditioning effect and also effectively simplifying the application treatment while providing sufficient effects, the composition is preferably a hair cleansing composition and more preferably a cleansing conditioner.

Regarding the above-described embodiment, the present invention further discloses the following cleansing compositions:

[1] A cleansing composition comprising the following components (A) to (C):

(A) an internal olefin sulfonate having 12 or more and 24 or less of carbon atoms: 1.8 mass % or more and 20 mass % or less;

(B) a cationic surfactant represented by the following formula (b-1) or (b-2): 0.1 mass % or more and 8 mass % or less,

wherein R¹ represents an aliphatic hydrocarbon group having 11 to 23 carbon atoms, R² represents a hydrogen atom or an alkyl group having 1 to 4 carbon atoms, and n represents an integer of 2 to 4,

wherein R³ represents a linear or branched alkyl group or alkenyl group having 10 to 22 carbon atoms, R⁴, R¹, and R⁶ each independently represent a linear or branched alkyl group having 1 to 3 carbon atoms, and Z– represents an anionic group being a counterion for an ammonium salt; and (C) an aliphatic alcohol having 12 or more and 22 or less of carbon atoms: 1 mass % or more and 20 mass % or less, wherein the mass ratio of the content of the component (B) to the content of the component (A), (B)/(A), is 0.1 or more and 1 or less, and the mass ratio of the content of the component (C) to the total content of the component (A) and the component (B), (C)/{(A)+(B)}, is 0.1 or more and 4.5 or less;

[2] A cleansing composition comprising the following components (A) to (C):

(A) an internal olefin sulfonate selected from the group consisting of internal olefin sulfonates having 16 carbon atoms or 18 carbon atoms and a mixture thereof: 1 mass % or more and 15 mass % or less;

(B) a cationic surfactant selected from the group consisting of dimethylaminoethylamide stearate and dimethylaminopropylamide stearate: 0.1 mass % or more and 8 mass % or less; and (C) an aliphatic alcohol selected from the group consisting of cetyl alcohol and stearyl alcohol and a mixture thereof: 1 mass % or more and 20 mass % or less, wherein the mass ratio of the content of the component (B) to the content of the component (A), (B)/(A), is 0.1 or more and 1 or less, and the mass ratio of the content of the component (C) to the total content of the component (A) and the component (B), (C)/{(A)+(B)}, is 0.1 or more and 4.5 or less;

[3] A cleansing composition comprising the following components (A) to (C):

(A) an internal olefin sulfonate selected from the group consisting of internal olefin sulfonates having 16 carbon atoms or 18 carbon atoms and a mixture thereof: 1.8 mass % or more and 20 mass % or less;

(B) a cationic surfactant being a mono long chain alkyl quaternary ammonium salt having 10 to 22 carbon atoms: 0.1 mass % or more and 8 mass % or less; and (C) an aliphatic alcohol selected from the group consisting of cetyl alcohol and stearyl alcohol and a mixture thereof: 1 mass % or more and 20 mass % or less, wherein the mass ratio of the content of the component (B) to the content of the component (A), (B)/(A), is 0.1 or more and 1 or less, and the mass ratio of the content of the component (C) to the total content of the component (A) and the component (B), (C)/{(A)+(B)}, is 0.1 or more and 4.5 or less;

[4] A cleansing composition comprising the following components (A) to (C):

(A) an internal olefin sulfonate selected from the group consisting of internal olefin sulfonates having 16 carbon atoms or 18 carbon atoms and a mixture thereof, where the total content of the internal olefin sulfonate having 16 carbon atoms and the internal olefin sulfonate having 18 carbon atoms in the component (A) is 50 mass % or more and 100 mass % or less: 1.8 mass % or more and 20 mass % or less;

(B) a cationic surfactant selected from the group consisting of dimethylaminoethylamide stearate and dimethylaminopropylamide stearate: 0.1 mass % or more and 8 mass % or less, (C) an aliphatic alcohol selected from the group consisting of cetyl alcohol and stearyl alcohol and a mixture thereof: 1 mass % or more and 20 mass % or less, wherein the mass ratio of the content of the component (B) to the content of the component (A), (B)/(A), is 0.1 or more and 1 or less, and the mass ratio of the content of the component (C) to the total content of the component (A) and the component (B), (C)/{(A)+(B)}, is 0.1 or more and 4.5 or less;

[5] A cleansing composition comprising the following components (A) to (C):

(A) an internal olefin sulfonate selected from the group consisting of internal olefin sulfonates having 16 carbon atoms or 18 carbon atoms and a mixture thereof, where the content of the internal olefin sulfonate having a sulfonate group at 2-position in the component (A) is 5 mass % or more and 25 mass % or less: 1.8 mass % or more and 20 mass % or less;

(B) a cationic surfactant selected from the group consisting of dimethylaminoethylamide stearate and dimethylaminopropylamide stearate: 0.1 mass % or more and 8 mass % or less; and (C) an aliphatic alcohol selected from the group consisting of cetyl alcohol and stearyl alcohol and a mixture thereof: 1 mass % or more and 20 mass % or less, wherein the mass ratio of the content of the component (B) to the content of the component (A), (B)/(A), is 0.1 or more and 1 or less, and the mass ratio of the content of the component (C) to the total content of the component (A) and the component (B), (C)/{(A)+(B)}, is 0.1 or more and 4.5 or less;

[6] A cleansing composition comprising the following components (A) to (C):

(A) an internal olefin sulfonate selected from the group consisting of internal olefin sulfonates having 16 carbon atoms or 18 carbon atoms and a mixture thereof, where the total content of the internal olefin sulfonate having 16 carbon atoms and the internal olefin sulfonate having 18 carbon atoms in the component (A) is 50 mass % or more and 100 mass % or less: 1.8 mass % or more and 20 mass % or less;

(B) a cationic surfactant being a mono long chain alkyl quaternary ammonium salt having 10 or more and 22 or less of carbon atoms: 0.1 mass % or more and 8 mass % or less; and (C) an aliphatic alcohol selected from the group consisting of cetyl alcohol and stearyl alcohol and a mixture thereof: 1 mass % or more and 20 mass % or less, wherein the mass ratio of the content of the component (B) to the content of the component (A), (B)/(A), is 0.1 or more and 1 or less, and the mass ratio of the content of the component (C) to the total content of the component (A) and the component (B), (C)/{(A)+(B)}, is 0.1 or more and 4.5 or less;

[7] A cleansing composition comprising the following components (A) to (C):

(A) an internal olefin sulfonate selected from the group consisting of internal olefin sulfonates having 16 carbon atoms or 18 carbon atoms and a mixture thereof, where the content of the internal olefin sulfonate having a sulfonate group at 2-position in the component (A) is 5 mass % or more and 25 mass % or less: 1.8 mass % or more and 20 mass % or less;

(B) a cationic surfactant being a mono long chain alkyl quaternary ammonium salt having 10 or more and 22 or less of carbon atoms: 0.1 mass % or more and 8 mass % or less; and (C) an aliphatic alcohol selected from the group consisting of cetyl alcohol and stearyl alcohol and a mixture thereof: 1 mass % or more and 20 mass % or less, wherein the mass ratio of the content of the component (B) to the content of the component (A), (B)/(A), is 0.1 or more and 1 or less, and the mass ratio of the content of the component (C) to the total content of the component (A) and the component (B), (C)/{(A)+(B)}, is 0.1 or more and 4.5 or less;

[8] A cleansing composition comprising the following components (A) to (C):

(A) an internal olefin sulfonate selected from the group consisting of internal olefin sulfonates having 16 carbon atoms or 18 carbon atoms and a mixture thereof, where the total content of the internal olefin sulfonate having 16 carbon atoms and the internal olefin sulfonate having 18 carbon atoms in the component (A) is 50 mass % or more and 100 mass % or less, and further the content of the internal olefin sulfonate having a sulfonate group at 2-position in the component (A) is 5 mass % or more and 25 mass % or less: 1.8 mass % or more and 20 mass % or less;

(B) a cationic surfactant selected from the group consisting of dimethylaminoethylamide stearate and dimethylaminopropylamide stearate: 0.1 mass % or more and 8 mass % or less; and (C) an aliphatic alcohol selected from the group consisting of cetyl alcohol and stearyl alcohol and a mixture thereof: 1 mass % or more and 20 mass % or less, wherein the mass ratio of the content of the component (B) to the content of the component (A), (B)/(A), is 0.1 or more and 1 or less, and the mass ratio of the content of the component (C) to the total content of the component (A) and the component (B), (C)/{(A)+(B)}, is 0.1 or more and 4.5 or less;

[9] A cleansing composition comprising the following components (A) to (C):

(A) an internal olefin sulfonate selected from the group consisting of internal olefin sulfonates having 16 carbon atoms or 18 carbon atoms and a mixture thereof, where the total content of the internal olefin sulfonate having 16 carbon atoms and the internal olefin sulfonate having 18 carbon atoms in the component (A) is 50 mass % or more and 100 mass % or less, and further the content of the internal olefin sulfonate having a sulfonate group at 2-position in the component (A) is 5 mass % or more and 25 mass % or less: 1.8 mass % or more and 20 mass % or less;

(B) a cationic surfactant being a mono long chain alkyl quaternary ammonium salt having 10 or more and 22 or less of carbon atoms: 0.1 mass % or more and 8 mass % or less; and (C) an aliphatic alcohol (C) selected from the group consisting of cetyl alcohol and stearyl alcohol and a mixture thereof: 1 mass % or more and 20 mass % or less, wherein the mass ratio of the content of the component (B) to the content of the component (A), (B)/(A), is 0.1 or more and 1 or less, and the mass ratio of the content of the component (C) to the total content of the component (A) and the component (B), (C)/{(A)+(B)}, is 0.1 or more and 4.5 or less;

[10] A cleansing composition comprising the following components (A) to (C):

(A) an internal olefin sulfonate selected from the group consisting of internal olefin sulfonates having 16 carbon atoms or 18 carbon atoms and a mixture thereof, where the total content of the internal olefin sulfonate having 16 carbon atoms and the internal olefin sulfonate having 18 carbon atoms in the component (A) is 50 mass % or more and 100 mass % or less, and the content of the internal olefin sulfonate having a sulfonate group at 2-position in the component (A) is 5 mass- or more and 25 mass % or less, and further the mass ratio of the content of the hydroxy form of the internal olefin sulfonate to the content of the olefin form of the internal olefin sulfonate, (hydroxy form)/(olefin form), in the component (A) is 75/25 to 100/0: 1.8 mass % or more and 20 mass % or less;

(B) a cationic surfactant selected from the group consisting of dimethylaminoethylamide stearate and dimethylaminopropylamide stearate: 0.1 mass % or more and 8 mass % or less; and (C) an aliphatic alcohol selected from the group consisting of cetyl alcohol and stearyl alcohol and a mixture thereof: 1 mass % or more and 20 mass % or less, wherein the mass ratio of the content of the component (B) to the content of the component (A), (B)/(A), is 0.1 or more and 1 or less, and the mass ratio of the content of the component (C) to the total content of the component (A) and the component (B), (C)/{(A)+(B)}, is 0.1 or more and 4.5 or less;

[11] A cleansing composition comprising the following components (A) to (C):

(A) an internal olefin sulfonate selected from the group consisting of internal olefin sulfonates having 16 carbon atoms or 18 carbon atoms and a mixture thereof, where the total content of the internal olefin sulfonate having 16 carbon atoms and the internal olefin sulfonate having 18 carbon atoms in the component (A) is 50 mass % or more and 100 mass % or less, the content of the internal olefin sulfonate having a sulfonate group at 2-position in the component (A) is 5 mass % or more and 25 mass % or less, and further the mass ratio of the content of the hydroxy form of the internal olefin sulfonate to the content of the olefin form of the internal olefin sulfonate, (hydroxy form)/(olefin form), in the component (A) is 75/25 to 100/0: 1.8 mass % or more and 20 mass % or less;

(B) a cationic surfactant being a mono long chain alkyl quaternary ammonium salt having 10 or more and 22 or less of carbon atoms: 0.1 mass % or more and 8 mass % or less; and (C) an aliphatic alcohol selected from the group consisting of cetyl alcohol and stearyl alcohol and a mixture thereof: 1 mass % or more and 20 mass % or less, wherein the mass ratio of the content of the component (B) to the content of the component (A), (B)/(A), is 0.1 or more and 1 or less, and the mass ratio of the content of the component (C) to the total content of the component (A) and the component (B), (C)/{(A)+(B)}, is 0.1 or more and 4.5 or less;

[12] The cleansing composition according to any one of [1] to [11], wherein the content of the component (A) is 1.8 to 20 mass % and preferably 2.0 to 5.5 mass %; the content of the component (B) is 0.1 to 8 mass %; and the content of the component (C) is 1 to 20 mass %;

[13] The cleansing composition according to any one of [1] to [11], wherein the content of the component (A) is 1.8 to 20 mass %; the content of the component (B) is 0.1 to 8 mass %, preferably 1.0 to 2.0 mass %, and more preferably 1.5 to 2.0 mass %; and the content of the component (C) is 1 to 20 mass %;

[14] The cleansing composition according to any one of [1] to [13], wherein the content of the component (C) is 1 mass % or more and 15 mass % or less;

[15] The cleansing composition according to any one of [1] to [14], wherein the mass ratio, (C)/{(A)+(B)}, is 0.1 or more and 3.5 or less;

[16] The cleansing composition according to any one of [1] to [15], wherein the content of the component (A) is 1.8 to 20 mass %; the content of the component (B) is 0.1 to 8 mass %; and the content of the component (C) is 1 to 15 mass %, preferably 2.4 to 15 mass %, more preferably 2.4 to 11 mass %, and further preferably 3.6 to 11 mass %;

[17] The cleansing composition according to any one of [1] to [15], wherein the content of the component (A) is 2.0 to 8.5 mass %; the content of the component (B) is 1.0 to 2.0 mass %; and the content of the component (C) is 2.4 to 15 mass %;

[18] The cleansing composition according to any one of [1] to [17], wherein the content of the component (C) is 2.4 to 11 mass %;

[19] The cleansing composition according to any one of [1] to [15], wherein the content of the component (A) is 2.0 to 5.5 mass %; the content of the component (B) is 1.5 to 2.0 mass %; and the content of the component (C) is 3.6 to 11 mass %;

[20] The cleansing composition according to any one of [1] to [19], wherein the mass ratio of the content of the component (B) to the content of the component (A), (B)/(A), is 0.1 or more and 1 or less, preferably 0.1 or more and 0.9 or less, and more preferably 0.3 or more and 0.9 or less; and the mass ratio, (C)/{(A)+(B)}, is 0.1 or more and 4.5 or less;

[21] The cleansing composition according to any one of [1] to [20], wherein the mass ratio of the content of the component (B) to the content of the component (A), (B)/(A), is 0.1 or more and 1 or less; and the mass ratio, (C)/{(A)+(B)}, is 0.5 to 3.5, preferably 0.9 to 3.3, and more preferably 0.9 to 2.4;

[22] The cleansing composition according to any one of [1] to [19], wherein the mass ratio of the content of the component (B) to the content of the component (A), (B)/(A), is 0.1 or more and 0.9 or less; and the mass ratio, (C)/{(A)+(B)}, is 0.5 or more and 3.5 or less;

[23] The cleansing composition according to any one of [1] to [22], wherein the mass ratio, (C)/{(A)+(B)}, is 0.5 or more and 2.4 or less;

[24] The cleansing composition according to any one of [1] to [19], wherein the mass ratio of the content of the component (B) to the content of the component (A), (B)/(A), is 0.3 or more and 0.9 or less; and the mass ratio, (C)/{(A)+(B)}, is 0.9 or more and 2.4 or less;

[25] The cleansing composition according to any one of [1] to [24], wherein the component (A) is an internal olefin sulfonate selected from the group consisting of internal olefin sulfonates having 16 carbon atoms or 18 carbon atoms and a mixture thereof;

[26] The cleansing composition according to any one of [1] to [25], wherein the total content of the internal olefin sulfonate having 16 carbon atoms and the internal olefin sulfonate having 18 carbon atoms in the component (A) is 50 mass % or more and 100 mass % or less;

[27] The cleansing composition according to any one of [1] to [26], wherein the content of the internal olefin sulfonate having a sulfonate group at 2-position in the component (A) is 5 mass % or more and 25 mass % or less;

[28] The cleansing composition according to any one of [1] to [27], wherein the mass ratio of the content of the hydroxy form of the internal olefin sulfonate to the content of the olefin form of the internal olefin sulfonate, (hydroxy form)/(olefin form), in the component (A) is 75/25 to 100/0;

[29] The cleansing composition according to any one of [1] to [28], wherein the component (B) is one or more cationic surfactants (b-1) selected from the group consisting of diethylaminoethylamide stearate and dimethylaminopropylamide stearate;

[30] The cleansing composition according to any one of [1] to [29], wherein the component (B) is a cationic surfactant (b-2) being a mono long chain alkyl quaternary ammonium salt having 10 to 22 carbon atoms;

[31] The cleansing composition according to any one of [1] to [30], wherein the component (C) is a cetyl alcohol, stearyl alcohol, or a mixture thereof;

[32] The cleansing composition according to any one of [1] to [31], wherein the content of the component (A) is preferably 2.0 to 8.5 mass % and more preferably 2.0 to 5.5 mass %;

[33] The cleansing composition according to any one of [1] to [32], wherein the content of the component (B) is preferably 1.0 to 2.0 mass % and more preferably 1.5 to 2.0 mass %;

[34] The cleansing composition according to any one of [1] to [33], wherein the content of the component (C) is preferably 2.4 to 11.0 mass % and more preferably 3.6 to 11.0 mass %;

[35] The cleansing composition according to any one of [1] to [34], wherein the mass ratio of the content of the component (B) to the content of the component (A), (B)/(A), is preferably 0.1 to 0.9 and more preferably 0.3 to 0.9;

[36] The cleansing composition according to any one of [1] to [35], wherein the mass ratio of the content of the component (C) to the total content of the component (A) and the component (B), (C)/{(A)+(B)}, is preferably 0.5 to 2.4 and more preferably 0.9 to 2.4;

[37] The cleansing composition according to any one of [1] to [36], where the composition preferably has a viscosity at 30° C. of 500 to 30,000 mPa·s, more preferably 10,000 mPa·s, and further preferably 1,000 to 5,000 mPa·s;

[38] The cleansing composition according to any one of [1] to [37], where the composition is preferably a skin cleansing composition selected from the group consisting of body shampoo, facial cleanser, a makeup remover, and hand soap or a hair cleansing composition selected from the group consisting of hair shampoo and a cleansing conditioner, more preferably a hair cleansing composition, and further preferably a cleansing conditioner;

[39] A method for washing hair, including applying the cleansing composition according to any one of [1] to [38] to hair and washing and then rinsing the hair;

17

[40] A method for washing skin, including applying the cleansing composition according to any one of [1] to [38] to skin and washing and then rinsing the skin;

[41] Use of the cleansing composition according to any one of [1] to [38] for imparting a cleansing effect and a conditioning effect to hair; and

[42] Use of the cleansing composition according to any one of [1] to [38] for imparting a cleansing effect and a skin care feeling to skin.

Examples

The present invention will now be specifically described based on examples. Unless specified otherwise in tables, the content of each component is indicated by mass %. Methods for measuring each physical property are as follows.

(1) Measurement Conditions (i) Method for Measuring the Position of Double Bond in Raw Material Internal Olefin The position of a double bond in the raw material internal olefin was measured by gas chromatography (hereinafter, abbreviated to CC). Specifically, a dithiolated derivative was obtained by reacting an internal olefin with dimethyl disulfide, and each component was then separated by GC. Based on the results, the position of the double bond in the internal olefin was determined from the respective peak areas.

The apparatus and analytical conditions used in the measurement are as follows. GC apparatus (trade name: HP6890, produced by Hewlett-Packard Company), Column (trade name: Ultra-Alloy-1HT capillary column, 30 m×250 μm×0.15 μm, produced by Frontier Laboratories Ltd.), Detector (hydrogen flame ionization detector (FID)), Injection temperature: 300° C., Detector temperature: 350° C., and He flow rate: 4.6 mL/min.

(ii) Method for Measuring Mass Ratio of Hydroxy Form/Olefin Form

The mass ratio of hydroxy form/olefin form of an internal olefin sulfonate was measured by HPLC-MS. Specifically, the hydroxy form and the olefin form were separated by HPLC and were each applied to MS for identification. Based on the results, the ratio of each was determined from the HPLC-MS peak areas.

The apparatus and the conditions used for the measurement are as follows. HPLC apparatus (trade name: Agilent Technologies 1100, produced by Agilent Technologies, Inc.), Column (trade name: L-column ODS, 4.6×150 mm, produced by Chemicals Evaluation and Research Institute, Japan), Sample preparation (1,000 times dilution with methanol), Eluent A (10 mM ammonium acetate added water), Eluent B (10 mM ammonium acetate added methanol), Gradient (0 min (A/B=30%/70%)→10 min (30%/70%)→55 min (0%/100%)→65 min (0%/100%)→66 min (30%/70%)→75 min (30%/70%)), MS apparatus (trade name: Agilent Technologies 1100 MS SL (G1946D)), and MS detector (anion detection: m/z 60-1600, UV: 240 nm).

(iii) Method for Measuring Content of Raw Material Internal Olefin

The content of the raw material internal olefin in an internal olefin sulfonate was measured by GC. Specifically, ethanol and petroleum ether were added to an internal olefin sulfonate aqueous solution, followed by extraction to obtain an olefin in the petroleum ether phase. Based on the results, the olefin amount was quantitatively determined from the GC peak area. The apparatus and analytical conditions used in the measurement are as follows. GC apparatus (trade name: Agilent Technologies 6850, produced by Agilent Technologies, Inc.), Column (trade name: Ultra-Alloy-1HT capillary column, 15 m×250 μm×0.15 μm, produced by Frontier Laboratories Ltd.), Detector (hydrogen flame ionization detector (FID)), Injection temperature: 300° C., Detector temperature: 350° C., and He flow rate: 3.8 mL/min.

(iv) Method for Measuring Content of Inorganic Compound

The content of an inorganic compound was measured by potentiometric titration or neutralization titration. Specifically, the content of $Na_2SO_4$ was quantitatively determined by potentiometric titration of sulfate radical ($SO_4^{2-}$). The content of NaOH was quantitatively determined by neutralization titration with dilute hydrochloric acid.

(v) Method for Measuring Content of Internal Olefin Sulfonate Having Sulfonate Group at 2-Position The binding position of a sulfonate group was measured by GC. Specifically, a methyl esterified derivative was obtained by reacting the resulting internal olefin sulfonate (A) with trimethylsilyldiazomethane, and each component was then separated by GC. The content of the internal olefin sulfonate having a sulfonate group at 2-position was calculated using each peak area ratio as the mass ratio.

The apparatus and analytical conditions used in the measurement are as follows. GC apparatus (trade name: Agilent Technologies 6850, produced by Agilent Technologies, Inc.), Column (trade name: HP-1 capillary column, 30 m×320 μm×0.25 μm, produced by Agilent Technologies, Inc.), Detector (hydrogen flame ionization detector (FID)), Injection temperature: 300° C., Detector temperature: 300° C., He flow rate: 1.0 mL/min, Oven (60° C. (0 min)→10° C./min→300° C. (10 min)).

(2) Production of Internal Olefin

Production Example A

1-Hexadecanol (product name: KALCOL 6098, produced by Kao Corporation, 7,000 g (28.9 mol)) and γ-alumina as a solid acid catalyst (STREM Chemicals, Inc., 700 g (10 wt % with respect to raw material alcohol)) were introduced in a flask equipped with a stirrer and were reacted at 280° C. with stirring while flowing nitrogen (7,000 mL/min) into the system for 3 hours. After completion of the reaction, the alcohol conversion rate was 100%, and the C16 internal olefin purity was 99.6%. The resulting crude internal olefin was transferred into a distillation flask and was distilled at 136° C. to 160° C./4.0 mmHg to obtain an internal olefin having 16 carbon atoms with an olefin purity of 100%. The double bond distribution in the resulting internal olefin was position C1: 0.8 mass %, position C2: 26.8 mass %, position C3: 22.6 mass %, position C4: 18.2 mass %, position C5: 16.5 mass %, position C6: 8.5 mass %, and the sum of positions C7 and C8: 6.6 mass %.

Production Example B

1-Octadecanol (product name: KALCOL 8098, produced by Kao Corporation, 7,000 g (25.9 mol)) and γ-alumina as a solid acid catalyst (STREM Chemicals, Inc., 700 g (10 wt % with respect to raw material alcohol)) were introduced in a flask equipped with a stirrer and were reacted at 280° C. with stirring while flowing nitrogen (7,000 mL/min) into the system for 10 hours. After completion of the reaction, the alcohol conversion rate was 100%, and the C18 internal olefin purity was 98.2%. The resulting crude internal olefin was transferred into a distillation flask and was distilled at internal temperature of 148° C. to 158° C./0.5 mmHg to obtain an internal olefin having 18 carbon atoms with an olefin purity of 100%. The double bond distribution in the resulting internal olefin was position C1: 0.5 mass %, position C2: 25.0 mass %, position C3: 22.8 mass %, position C4: 19.1 mass %, position C5: 14.0 mass %, position C6: 7.4 mass %, position C7: 5.4 mass %, and the sum of positions C8 and C9: 5.8 mass %.

Production Example C

The internal olefin having 16 carbon atoms (11.9 kg) obtained by the method of the production example A and the internal olefin having 18 carbon atoms (3.1 kg) obtained in the production example B were mixed with each other to obtain 15.0 kg of internal olefin having 16 and 18 carbon atoms (mass ratio: 79.4/20.6). The double bond distribution in this internal olefin was position C1: 0.7 mass %, position C2: 25.2 mass %, position C3: 21.6 mass %, position C4: 18.0 mass %, position C5: 16.2 mass %, position C6: 9.3 mass %, position C7: 4.4 mass %, position C8: 3.6 mass %, and position C9: 1.0 mass %.

Production Example D

An internal olefin having 16 carbon atoms with an olefin purity of 100% was prepared by adjusting the reaction time in the method of the production example A. The double bond distribution of the resulting internal olefin was position C1: 1.8 mass %, position C2: 30.4 mass %, position C3: 23.9 mass %, position C4: 16.8 mass %, position C5: 12.0 mass %, position C6: 7.4 mass %, and the sum of positions C7 and C8: 7.8 mass %.

Production Example E

An internal olefin having 18 carbon atoms with an olefin purity of 100% was prepared by adjusting the reaction time in the method of the production example B. The double bond distribution of the resulting internal olefin was position C1: 0.5 mass %, position C2: 25.0 mass %, position C3: 22.8 mass %, position C4: 19.1 mass %, position C5: 14.0 mass %, position C6: 7.4 mass %, position C7: 5.4 mass %, and the sum of positions C8 and C9: 5.8 mass %.

(3) Production of Internal Olefin Sulfonate

Production Example 1: Production of Sodium Internal Olefin Sulfonate (1)

The internal olefin (the content of internal olefin having a double bond at 2-position is 25.2 mass %) having 16 or 18 carbon atoms produced in production example C was placed in a thin-film sulfonation reactor (internal diameter: 14 mm, length: 4 m) and was sulfonated using a sulfur trioxide gas containing 2.8 vol % of $SO_3$ concentration under conditions of passing cooling water of 20° C. through the outer jacket of the reactor. The $SO_3$/internal olefin reaction molar ratio was set to 1.09. The resulting sulfonated product was added to an alkali aqueous solution prepared by adding sodium hydroxide in an amount of 1.2 mol times the theoretical acid value (AV), followed by neutralization while stirring at 30° C. for 1 hour. The neutralized product was hydrolyzed by heating in an autoclave at 160° C. for 1 hour to obtain a crude product of sodium C16/18 internal olefin sulfonate.

The resulting crude product (300 g) was transferred in a separatory funnel, ethanol (300 mL) was added thereto, and petroleum ether (300 mL) was then added per time to extract and remove oil-soluble impurities. On this occasion, the inorganic compounds (of which the main component was mirabilite) precipitated at the oil/water interface by addition of ethanol were also separated and removed from the aqueous phase by the oil-water separation procedure, and this procedure was repeated three times. The aqueous phase side was evaporated to dryness to obtain sodium internal olefin sulfonates having 16 or 18 carbon atoms.

The mass ratio of hydroxy form (sodium hydroxyalkane sulfonate)/olefin form (sodium olefin sulfonate) in the resulting sodium internal olefin sulfonate was 87/13. The content of the raw material internal olefin contained in the resulting sodium internal olefin sulfonate was less than 100 ppm (less than GC detection limit), and the content of inorganic compounds was 0.5 mass %.

Production Example 2: Production of Sodium Internal Olefin Sulfonate (2)

A sodium internal olefin sulfonate having 16 carbon atoms was prepared using the internal olefin having 16 carbon atoms produced in production example D as the starting material under the same conditions as in production example 1. The content of the raw material internal olefin was less than 100 ppm (less than GC detection limit), and the content of inorganic compounds was 1.9 mass %.

Production Example 3: Production of Sodium Internal Olefin Sulfonate (3)

A sodium internal olefin sulfonate (7) having 18 carbon atoms was prepared under the same conditions as in production example 1 except that the internal olefin having 18 carbon atoms produced in the production example E was used. The content of the raw material internal olefin was less than 100 ppm (less than GC detection limit), and the content of inorganic compounds was 0.1 mass %.

These results are shown in Table 1.

TABLE 1

|  | Raw material internal olefin | | Internal olefin sulfonate | |
|---|---|---|---|---|
|  | Number of carbon atoms | Double bond at 2-Position (%) | HAS/IOS (mass ratio) | Content of internal olefin sulfonate having sulfonate group at 2-position (%) |
| Internal olefin sulfonate (1) (active component in production example 1) | C16/C18 | 25.2 | 87/13 | 17.6 |
| Internal olefin sulfonate (2) (active component in production example 2) | C16 | 30.4 | 80/20 | 20.3 |
| Internal olefin sulfonate (3) (active component in production example 3) | C18 | 25.0 | 80/20 | 15.0 |

Examples 1 to 23 and Comparative Examples 1 to 9

Each cleansing composition was prepared appropriately using the internal olefin sulfonates shown in Table 1 according to the prescriptions shown in Tables 2 to 6. Specifically, component (B) was dissolved in water warmed to 80° C. in a beaker, and component (A) or a surfactant other than component (A) was then added thereto, followed by mixing. The mixture was adjusted to about pH 4 with lactic acid as a pH adjuster.

Subsequently, component (C) was added to the mixture, followed by homogeneously mixing with a homomixer at 7,000 rpm for 2 minutes. Finally, the mixture was cooled to room temperature with stirring with a propeller at 300 rpm to manufacture each cleansing composition.

The resulting cleansing compositions were each subjected to measurement and evaluation according to the following methods.

Water of 15° dH (about 267 mg/L) was prepared using $CaCl_2$ (anhydrous) and $MgCl_2 \cdot 6H_2O$ by adjusting the ratio of Ca/Mg to 8/2 (=2.1 mM/0.53 mM).

The results are shown in Tables 2 to 6.

<<Measurement of Viscosity>>

Each cleansing composition was placed in a glass bottle and was left to stand at 30° C., and the viscosity (rotor No. 4, 30 rpm, after 1 minute) was then measured with a B-type viscometer. (TVB-10, Toki Sangyo Co., Ltd.).

<<Evaluation of Stability>>

Each cleansing composition was placed in a glass bottle and was left to stand at room temperature (25° C.) and also in a thermostat of 50° C. One month later, a cleansing composition which was not separated at room temperature but separated at 50° C. was evaluated as A, a cleansing composition which was separated into two phases at room temperature and 50° C. was evaluated as C, and a cleansing composition which was not separated at both room temperature and 50° C. was evaluated as AA.

<<Measurement of Foam Volume X>>

An aqueous solution (150 mL) of each cleansing composition diluted 30-fold with water of 150 dH was prepared, was stirred with a mixer (MX-X58, Panasonic Corporation) at 11,000 rpm for 10 seconds, and was then placed in a graduated cylinder, and the volume of foam was measured 30 seconds later as the foam volume (mL).

<<Measurement of Foam Volume Y>>

An aqueous solution (150 mL) of each cleansing composition diluted 30-fold with deionized water was prepared, was stirred with a mixer (MX-X58, Panasonic Corporation) at 11,000 rpm for 10 seconds, and was then placed in a graduated cylinder, and the volume of foam was measured 30 seconds later as the foam volume (mL).

<<Evaluation of Care Feeling (Feel) in Hair>>

Ten special panelists applied 1 g of each cleansing composition with water of 15° dH to each evaluation tress (length: about 30 cm, Caucasian hair: about 20 g), washed, and then rinsed the tress with the above-mentioned water for 30 seconds. Subsequently, the tress was blow-dried for 3 minutes, and then the slipperiness of the hair after drying and the softness of the hair after drying were evaluated according to the following criteria, and the average of the results of all panelists was determined and used as the index for the evaluation.

—Slipperiness of Hair after Drying
5: Slipperiness of hair after drying is very good;
4: Slipperiness of hair after drying is good;
3: Slipperiness of hair after drying are normal;
2: Slipperiness of hair after drying is low; and
1: Slipperiness of hair after drying is very low.

—Softness of Hair after Drying
5: Hair after drying is very soft;
4: Hair after drying is soft;
3: Softness of hair after drying is normal;
2: Hair after drying is hard; and
1: Hair after drying is very hard.

<<Evaluation of Cleansing Feel (Feeling after Cleansing) in Hair>>

Ten special panelists applied 1 g of each cleansing composition with water of 150 dH to each evaluation tress (length: about 30 cm, Caucasian hair: about 20 g), washed, and then rinsed the tress with the above-mentioned water for 30 seconds. Subsequently, the tress was dried with towel, and then the cleansing feel (feeling after cleansing) was evaluated by the fresh feeling after towel drying according to the following criteria, and the average of the results of all panelists was determined and used as the index for the evaluation.

5: Fresh feeling after towel drying is very good;
4: Fresh feeling after towel drying is good;
3: Fresh feeling after towel drying is normal;
2: Fresh feeling after towel drying is bad; and
1: Fresh feeling after towel drying is very bad.

TABLE 2

|   |   | Example 1 | Comparative Example 1 | Comparative Example 2 | Comparative Example 3 | Comparative Example 4 |
|---|---|---|---|---|---|---|
| (A) | Internal olefin sulfonate (1) (active component in production example 1) | 4.0 |   |   |   | 4.0 |
|   | Sodium polyoxyethylene lauryl ether sulfate *1 |   | 4.0 |   |   |   |
|   | Cocamidopropyl betaine *2 |   |   | 4.0 |   |   |
|   | Lauryl glucoside *3 |   |   |   | 4.0 |   |
| (B) | Dimethylaminopropylamide stearate *4 | 1.5 | 1.5 | 1.5 | 1.5 | 1.5 |
| (C) | Cetostearyl alcohol *5 | 10.0 | 10.0 | 10.0 | 10.0 | — |
|   | pH adjuster (lactic acid) | Amount for adjusting to pH 4 | | | | |
|   | Purified water | Balance | | | | |
|   | Total | 100.0 | 100.0 | 100.0 | 100.0 | 100.0 |
|   | (C)/{(A) + (B)} | 1.8 | 1.8 | 1.8 | 1.8 | — |
|   | (B)/(A) | 0.375 | 0.375 | 0.375 | 0.375 | 0.375 |
|   | Viscosity (mPa · s) | 3030 | 2630 | Separated | Separated | 398 |

TABLE 2-continued

|  | | Example 1 | Comparative Example 1 | Comparative Example 2 | Comparative Example 3 | Comparative Example 4 |
|---|---|---|---|---|---|---|
| Evaluation | Stability | AA | AA | C | C | A |
| | Foam volume X (mL) | 330 | 260 | — | 220 | 120 |
| | Foam volume Y (mL) | 490 | 430 | | | |
| | Care feeling (Slipperiness of hair after drying) | 3.6 | 2.4 | 2.9 | 3.2 | 1.2 |
| | Care feeling (Softness of hair after drying) | 3.4 | 2.0 | 3.1 | 2.5 | 1.4 |
| | Cleansing feel | 3.5 | 2.8 | 2.4 | 2.1 | 3.0 |

[1] EMAL 270J, Kao Corporation
[2] AMPHITOL 55AB, Kao Corporation
[3] MYDOL 12, Kao Corporation
[4] Amidoamine MPS, Nikko Chemicals Co., Ltd.
[5] KALCOL 6850, Kao Corporation The cleansing compositions shown in Table 2 were further evaluated for the cleansing feel in skin.

Specifically, about 1 g of each cleansing composition was applied to each nylon towel (Kikulon Body Towel Awa Star) with water of 15° dH and frothed, and the feel when the forearm was washed with each cleansing composition was evaluated using an aqueous solution of 4% sodium polyoxyethylene lauryl ether sulfate (EMAL 270J, Kao Corporation) as a standard cleanser.

As a result, in Example 1, a washing effect equivalent to that of the standard cleanser was obtained, the skin after washing was moistened, and such a feeling continued. In contrast, in all Comparative Examples 1 to 3, no washing effect was felt, and no moist feel was also given to the skin after washing. In Comparative Example 4, although a washing effect was obtained, no moist feel was given to the skin after washing.

TABLE 3

|  |  | Example 1 | Example 2 | Example 3 | Example 4 | Example 5 | Example 6 |
|---|---|---|---|---|---|---|---|
| (A) | Internal olefin sulfonate (1) (active component in production example 1) | 4.0 | 2.1 | 2.6 | 3.0 | 5.5 | 11.0 |
| (B) | Dimethylaminopropylamide stearate [4] | 1.50 | 1.50 | 1.50 | 1.50 | 1.50 | 1.50 |
| (C) | Cetostearyl alcohol [5] | 10.0 | 7.9 | 9.4 | 11.0 | 8.5 | 3.0 |
| | pH adjuster (lactic acid) | Amount for adjusting to pH 4 | | | | | |
| | Purified water | Balance | | | | | |
| | Total | 100.00 | 100.00 | 100.00 | 100.00 | 100.00 | 100.00 |
| | (C)/{(A) + (B)} | 1.8 | 2.2 | 2.3 | 2.4 | 1.2 | 0.2 |
| | (B)/(A) | 0.375 | 0.714 | 0.577 | 0.500 | 0.273 | 0.136 |
| Evaluation | Stability | AA | AA | AA | AA | A | A |
| | Foam volume X (mL) | 330 | 290 | 320 | 340 | 290 | 530 |
| | Care feeling (Slipperiness of hair after drying) | 3.6 | 3.7 | 3.6 | 2.9 | 3.6 | 3.0 |
| | Care feeling (Softness of hair after drying) | 3.4 | 3.4 | 3.4 | 3.1 | 3.5 | 2.7 |

|  |  | Comparative Example 5 | Comparative Example 6 | Comparative Example 7 | Comparative Example 8 | Comparative Example 9 |
|---|---|---|---|---|---|---|
| (A) | Internal olefin sulfonate (1) (active component in production example 1) | 1.5 | 3.0 | 1.5 | 3.0 | 14.0 |
| (B) | Dimethylaminopropylamide stearate [4] | 0.75 | 4.00 | 0.75 | 1.50 | 1.50 |
| (C) | Cetostearyl alcohol [5] | 10.0 | 11.0 | 5.0 | 22.0 | 1.0 |
| | pH adjuster (lactic acid) | Amount for adjusting to pH 4 | | | | |
| | Purified water | Balance | | | | |
| | Total | 100.00 | 100.00 | 100.00 | 100.00 | 100.00 |
| | (C)/{(A) + (B)} | 4.44 | 1.57 | 2.22 | 4.89 | 0.065 |
| | (B)/(A) | 0.500 | 1.333 | 0.500 | 0.500 | 0.107 |
| Evaluation | Stability | C | C | C | C | A |
| | Foam volume X (mL) | — | — | — | 100 | 130 |
| | Care feeling (Slipperiness of hair after drying) | — | — | — | 1.3 | 1.3 |
| | Care feeling (Softness of hair after drying) | — | — | — | 1.5 | 1.4 |

[4] and [5] the same as those in Table 2

TABLE 4

|  |  | Example 4 | Example 7 | Example 8 | Example 9 | Example 10 |
|---|---|---|---|---|---|---|
| (A) | Internal olefin sulfonate (1) (active component in production example 1) | 3.0 | 3.0 | 3.0 | 3.0 | 3.0 |
| (B) | Dimethylaminopropylamide stearate [4] | 1.5 | | | | |
| | Dimethylaminopropylamide behenate [6] | | 1.5 | | | |

TABLE 4-continued

|  |  | Example 4 | Example 7 | Example 8 | Example 9 | Example 10 |
|---|---|---|---|---|---|---|
|  | Cetyltrimethylammonium chloride *7 |  |  | 1.5 |  |  |
|  | Stearyltrimethylammonium chloride *8 |  |  |  | 1.5 |  |
|  | Behenyltrimethylammonium chloride *9 |  |  |  |  | 1.5 |
| (C) | Cetostearyl alcohol *5 | 11.0 | 11.0 | 11.0 | 11.0 | 11.0 |
|  | pH adjuster (lactic acid) | Amount for adjusting to pH 4 | | | | |
|  | Purified water | Balance | | | | |
|  | Total | 100.0 | 100.0 | 100.0 | 100.0 | 100.0 |
|  | (C)/{(A) + (B)} | 2.4 | 2.4 | 2.4 | 2.4 | 2.4 |
|  | (B)/(A) | 0.5 | 0.5 | 0.5 | 0.5 | 0.5 |
| Evaluation | Stability | AA | AA | AA | AA | AA |
|  | Foam volume X (mL) | 340 | 330 | 320 | 320 | 320 |
|  | Care feeling (Slipperiness of hair after drying) | 2.9 | 2.9 | 2.8 | 3.1 | 3.2 |
|  | Care feeling (Softness of hair after drying) | 3.1 | 3.2 | 2.8 | 3.0 | 3.3 |

*4 and *5 the same as those in Table 2
*6 AMIDET APA22, Kao Corporation
*7 QUARTAMIN 60W, Kao Corporation
*8 QUARTAMIN 86W, Kao Corporation
*9 QUARTAMIN 2285EE, Kao Corporation

TABLE 5

|  |  | Example 1 | Example 11 | Example 12 |
|---|---|---|---|---|
| (A) | Internal olefin sulfonate (1) (active component in production example 1) | 4.0 |  |  |
|  | Internal olefin sulfonate (2) (active component in production example 2) |  | 4.0 |  |
|  | Internal olefin sulfonate (3) (active component in production example 3) |  |  | 4.0 |
| (B) | Dimethylaminopropylamide stearate *4 | 1.5 | 1.5 | 1.5 |
| (C) | Cetostearyl alcohol *5 | 10.0 | 10.0 | 10.0 |
|  | pH adjuster (lactic acid) | Amount for adjusting to pH 4 | | |
|  | Purified water | Balance | | |
|  | Total | 100.0 | 100.0 | 100.0 |
|  | (C)/{(A) + (B)} | 1.8 | 1.8 | 1.8 |
|  | (B)/(A) | 0.375 | 0.375 | 0.375 |
|  | Viscosity (mPa · s) | 3030 | 2980 | 3140 |
| Evaluation | Stability | AA | AA | AA |
|  | Foam volume X (mL) | 330 | 340 | 300 |
|  | Care feeling (Slipperiness of hair after drying) | 3.6 | 3.3 | 3.6 |
|  | Care feeling (Softness of hair after drying) | 3.4 | 3.2 | 3.8 |
|  | Cleansing feel | 3.5 | 3.6 | 3.0 |

*4 and *5 the same as those in Table 2

TABLE 6

|  |  | Example 13 | Example 14 | Example 15 | Example 16 | Example 17 | Example 18 |
|---|---|---|---|---|---|---|---|
| (A) | Internal olefin sulfonate (1) (active component in production example 1) | 4.0 | 1.8 | 4.0 | 3.0 | 3.0 | 3.0 |
| (B) | Dimethylaminopropylamide stearate *4 | 3.80 | 1.50 | 1.00 | 0.75 | 1.50 | 1.50 |
| (C) | Cetostearyl alcohol *5 | 10.0 | 8.0 | 10.0 | 8.0 | 13.0 | 18.0 |
|  | Stearyl alcohol *10 |  |  |  |  |  |  |
|  | Behenyl alcohol *11 |  |  |  |  |  |  |
|  | pH adjuster (lactic acid) | Amount for adjusting to pH 4 | | | | | |
|  | Purified water | Balance | | | | | |
|  | Total | 100.00 | 100.00 | 100.00 | 100.00 | 100.00 | 100.00 |
|  | (C)/{(A)+(B)} | 1.3 | 2.4 | 2.0 | 2.1 | 2.9 | 4.0 |
|  | (B)/(A) | 0.95 | 0.80 | 0.25 | 0.25 | 0.50 | 0.50 |
| Evaluation | Viscosity (mPa · s) |  |  |  |  | 20,300 | 21,300 |
|  | Stability | A | AA | A | AA | AA | AA |
|  | Foam volume X (mL) | 220 | 280 | 210 | 205 | 355 | 340 |
|  | Care feeling (Slipperiness of hair after drying) | 2.5 | 2.7 | 2.6 | 2.6 | 3.4 | 3.0 |
|  | Care feeling (Softness of hair after drying) | 2.9 | 2.9 | 2.5 | 2.6 | 3.6 | 3.1 |

TABLE 6-continued

|  |  | Example 19 | Example 20 | Example 21 | Example 22 | Example 23 |
|---|---|---|---|---|---|---|
| (A) | Internal olefin sulfonate (1) (active component in production example 1) | 3.0 | 3.0 | 2.0 | 4.0 | 4.0 |
| (B) | Dimethylaminopropylamide stearate *4 | 1.50 | 1.50 | 1.00 | 1.50 | 1.50 |
| (C) | Cetostearyl alcohol *5 | 20.0 | 15.0 | 10.5 | | |
|  | Stearyl alcohol *10 | | | | 10.0 | 5.0 |
|  | Behenyl alcohol *11 | | | | | 5.0 |
|  | pH adjuster (lactic acid) | Amount for adjusting to pH 4 | | | | |
|  | Purified water | Balance | | | | |
|  | Total | 100.00 | 100.00 | 100.00 | 100.00 | 100.00 |
|  | (C)/{(A)+(B)} | 4.4 | 3.3 | 3.5 | 1.8 | 1.8 |
|  | (B)/(A) | 0.50 | 0.50 | 0.50 | 0.38 | 0.38 |
| Evaluation | Viscosity (mPa · s) | 26,200 | 17,200 | | | |
|  | Stability | A | AA | A | AA | AA |
|  | Foam volume X (mL) | 330 | 360 | 245 | 200 | 230 |
|  | Care feeling (Slipperiness of hair after drying) | 3.0 | 3.1 | 3.1 | 3.3 | 3.5 |
|  | Care feeling (Softness of hair after drying) | 2.5 | 3.5 | 2.5 | 3.7 | 3.9 |

*4 and *5 the same as those in Table 2
*10 KALCOL 8098, Kao Corporation
*11 KALCOL 220-80, Kao Corporation

The invention claimed is:

1. A cleansing composition comprising the following components (A) to (C):
(A) 1.8 mass % or more and 20 mass % or less of at least one internal olefin sulfonate having 12 or more and 24 or less of carbon atoms;
(B) 0.1 mass % or more and 8 mass % or less of a cationic surfactant represented by the following formula (b-1) or (b-2), $$R^1CONH(CH_2)_nN(R^2)_2 \quad (b\text{-}1)$$

wherein $R^1$ represents an aliphatic hydrocarbon group having 11 to 23 carbon atoms; $R^2$ represents a hydrogen atom or an alkyl group having 1 to 4 carbon atoms; and n represents an integer of 2 to 4, $$\left[ \begin{array}{c} R^4 \\ | \\ R^3 - N^+ - R^6 \\ | \\ R^5 \end{array} \right] Z^- \quad (b\text{-}2)$$

wherein $R^3$ represents a linear or branched alkyl group or alkenyl group having 10 to 22 carbon atoms; $R^4$, $R^5$, and $R^6$ each independently represent a linear or branched alkyl group having 1 to 3 carbon atoms; and $Z^-$ represents an anionic group being a counterion for an ammonium salt; and
(C) 1 mass % or more and 20 mass % or less of an aliphatic alcohol having 12 or more and 22 or less of carbon atoms, wherein
a mass ratio of a content of the component (B) to a content of the component (A), (B)/(A), is 0.1 or more and 1 or less; and
a mass ratio of a content of the component (C) to a total content of the component (A) and the component (B), (C)/{(A)+(B)}, is 0.1 or more and 4.5 or less.

2. The cleansing composition according to claim 1, having a total content of the at least one internal olefin sulfonate includes an internal olefin sulfonate having 16 carbon atoms and an internal olefin sulfonate having 18 carbon atoms in the component (A) of 50 mass % or more and 100 mass % or less.

3. The cleansing composition according to claim 1, having a content of the at least one internal olefin sulfonate includes an internal olefin sulfonate having a sulfonate group at 2-position, in the component (A) of 5 mass % or more and 40 mass % or less.

4. The cleansing composition according to claim 1, having a mass ratio of hydroxy form of internal olefin sulfonate to olefin form of internal olefin sulfonate, (hydroxy form)/(olefin form), in component (A) is 50/50 to 100/0.

5. The cleansing composition according to claim 1, having a content of an anionic surfactant other than the component (A) of less than 10 mass %.

6. The cleansing composition according to claim 1, wherein the cleansing composition has a viscosity at 30° C. is 500 to 30,000 mPa·s.

7. The cleansing composition according to claim 1, wherein the component (b-1) is one or more selected from the group consisting of dimethylaminoethylamide stearate, dimethylaminopropylamide stearate, diethylaminoethylamide stearate, diethylaminopropylamide stearate, dipropylaminoethylamide stearate, dipropylaminopropylamide stearate, dimethylaminoethylamide palmitate, dimethylaminopropylamide palmitate, dimethylaminoethylamide myristate, dimethylaminopropylamide myristate, dimethylaminoethylamide behenate, and dimethylaminopropylamide behenate.

8. The cleansing composition according to claim 1, wherein the component (b-2) is a mono long chain alkyl quaternary ammonium salt having 10 to 22 carbon atoms.

9. The cleansing composition according to claim 1, wherein the component (C) is one or more selected from the group consisting of cetyl alcohol, stearyl alcohol, arachyl alcohol, and behenyl alcohol.

10. The cleansing composition according to claim 1, which is used for washing skin or hair.

11. A method for washing skin or hair, the method comprising applying the cleansing composition according to claim 1 to skin or hair, followed by washing and then rinsing.

* * * * *